United States Patent [19] [11] Patent Number: 4,948,903
Navarrini et al. [45] Date of Patent: Aug. 14, 1990

[54] PERFLUORODIAZIRIDINES AND PROCESS FOR PREPARING THEM

[75] Inventors: Walter Navarrini, Boffalora, Italy; Darryl D. Desmarteau, Clemson, S.C.

[73] Assignee: Ausimont S.r.l., Milan, Italy

[21] Appl. No.: 369,046

[22] Filed: Jun. 19, 1989

[30] Foreign Application Priority Data

Jun. 22, 1988 [IT] Italy ................. 21063 A/88

[51] Int. Cl.$^5$ ......................... C07D 229/02
[52] U.S. Cl. .................................. 548/960
[58] Field of Search ......................... 548/960

[56] References Cited

U.S. PATENT DOCUMENTS 3,345,360 10/1967 Firth ...................... 548/960

*Primary Examiner*—Mukund J. Shah
*Assistant Examiner*—C. L. Cseh

*Attorney, Agent, or Firm*—Stevens, Davis, Miller & Mosher

[57] ABSTRACT

Novel perfluorodiazyridiness having the formula:

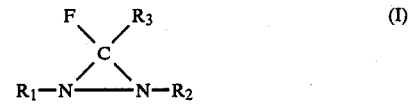

wherein:
$R^1$ and $R_2$, alike or different from each other, represent a perfluoroalkyl group of from 1 to 10 carbon atoms, and
$R_3$ represents a fluorine atom, or a perfluoroalkyl group of from 1 to 9 carbon atoms.

These perfluorodiaziridines are obtained by reacting perfluoroaminooxaziridines with a source of fluoride ions.

2 Claims, No Drawings

PERFLUORODIAZIRIDINES AND PROCESS FOR PREPARING THEM

DESCRIPTION OF THE INVENTION

The present inventions relates to novel perfluorodiaziridines and to a process for preparing them.

Perfluorodiaziridines are a not very widely known class of organic compounds.

The perfluorodiaziridine of formula:

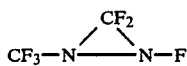

is known. This was synthesized by starting from $CF_2=N-F$ and CsF (Shi-Ching Chang and Darryl D. DesMarteau, J. Org. Chem. 1983, 48, 771-774).

One purpose of the present invention is to provide a novel class of perfluorodiaziridines. A further purpose is to provide a process for preparing them.

The first purpose is achieved by providing the novel perfluorodiaziridines according to the present invention having the formula:

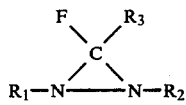

wherein:

$R_1$ and $R_2$, alike or different from each other, represent a perfluoroalkyl group of from 1 to 10 carbon atoms, and $R_3$ represents a fluorine atom, or a perfluoroalkyl group of from 1 to 9 carbon atoms.

These novel perfluorodiaziridines are useful as catalysts for the photochemical polymerization of olefinic monomers. They form complexes with transition metal ions, and are useful as intermediates in the preparation of nitrenes.

Preferably, $R_1$ and $R_2$ are perfluoroalkyl groups of from 1 to 3 carbon atoms, and $R_3$ is a fluorine atom, or a perfluoroalkyl group of from 1 to 2 carbon atoms.

These new perfluorodiaziridines may be prepared by reacting a perfluoroamino-oxaziridine of formula:

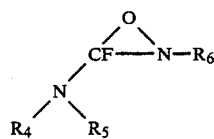

wherein: $R_4$, $R_5$ and $R_6$, alike or different from one another, are perfluoroalkyl groups containing from 1 to 10 carbon atoms, with a source of fluoride ions.

The reaction may be schematically shown as follows:

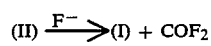

The $R_3$ radical of (I) derives from the $R_4$ or $R_5$ radical of (II), and contains one carbon atom less than this latter, so that $R_3$ is F when its source radical is $-CF_3$.

The $R_1$ and $R_2$ radicals of (I) derive from radicals of (II) different from the radical which supplied the $R_3$.

The reaction is commonly carried out at a temperature within the range of from 0° to 120° C.

As the fluoride ion sources, in particular, CsF, KF and tetraalkyl-ammonium fluorides are used.

The molar ratio of the fluoride ion source, computed as CsF, to the perfluoroaminooxaziridines (II) is generally within the range of from 0.1 to 10, and preferably from 1 to 10.

The reaction may be carried out in the presence of a dipolar aprotic solvent, such as acetonitrile, the glymes, dimethylformamide, and dimethylsulphoxide.

The perfluoroaminooxaziridines (II) and the process for preparing them are disclosed in U.S. Pat. No. 4,874,875, which is incorporated herein by reference.

According to that patent, perfluoroaminooxaziridines (II) are obtained by reacting a perfluoroimine of formula:

wherein $R_4$, $R_5$ and $R_6$ have the above meanings, with $H_2O_2$ in the presence of a base, in a dipolar aprotic solvent, at a temperature within the range of from $-50°$ to $+50°$ C.

The following example is provided as illustrative and not limitative of the present invention.

EXAMPLE

To a 150 ml glass reactor containing 3 g of CsF, 5 mmol is charged of a perfluoroaminooxaziridine of formula:

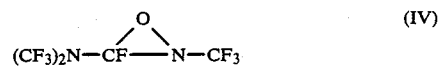

The so-charged reactor is maintained at room temperature for 8 hours.

The raw reaction product is distilled under a pressure of $10^{-3}$ torr.

The vapors from the distillation kettle flow through cold traps maintained at a temperature of $-120°$ C. and of $-196°$ C., respectively.

Inside the trap at $-120°$ C. 3 mmol condenses of 1,2-trifluoromethyl-3,3-difluorodiaziridine having the formula:

with a yield of 60% relative to the perfluoroaminooxaziridine used as the starting material. Inside the trap a mixture condenses at $-196°$ C. which is prevailingly constituted by $COF_2$, together with byproducts.

The diaziridine (V) was analyzed by I.R. spectrum, $^{19}F$ N.M.R., and mass spectrum.

The main absorption bands in the I.R. range are the following: $cm^{-1}$ (intensity): 1443 (s), 1317 (vs), 1277 (s), 1245 (vs), 1205 (s) and 996 (m), wherein "vs" stands for "very strong", "s" stands for "strong" and "m" stands for "medium."

The N.M.R. spectrum (internal reference $CFCl_3$; solvent $CdCl_3$), gave:

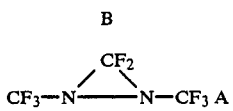

A = (triplet) - 65.6 ppm JAB 8 Hz
B = (heptet) - 108.6 ppm JAB 8 Hz

The mass spectrum gave:
M,216 (1.8%); 69 (100%); 128 (31.3%); 197 (19.1%).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A perfluorodiaziridine having the formula:

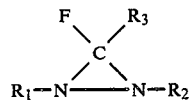

wherein:
  $R_1$ and $R_2$, alike or different from each other, represent a perfluoroalkyl group of from 1 to 3 carbon atoms, and
  $R_3$ represents a fluorine atom, or a perfluoroalkyl group of from 1 to 2 carbon atoms.

2. 1,2-trifluoromethyl-3,3-difluorodiaziridine having the formula:

* * * * *